United States Patent [19]
Acton et al.

[11] 3,976,884
[45] Aug. 24, 1976

[54] METHOD FOR REMOTE MONITORING OF GASEOUS PRODUCTS

[75] Inventors: Lawrence Lee Acton; Ervin Roy Bartle, Jr.; Gordon Dennis Hall, all of San Diego, Calif.

[73] Assignee: Science Applications, Inc., La Jolla, Calif.

[22] Filed: Dec. 31, 1974

[21] Appl. No.: 537,696

[52] U.S. Cl. ................................. 250/343; 356/97
[51] Int. Cl.² ....................................... G01M 21/26
[58] Field of Search ........... 250/343, 344, 345, 346, 250/373; 356/93, 95, 97

[56] References Cited
UNITED STATES PATENTS

| | | | |
|---|---|---|---|
| 3,558,229 | 1/1971 | Karle | 356/95 |
| 3,598,994 | 8/1971 | Markle | 356/97 |

Primary Examiner—Craig E. Church
Attorney, Agent, or Firm—Bruno J. Verbeck

[57] ABSTRACT

A method for remotely monitoring the concentration of a particular gas species in a gaseous mixture. The remote detection of pollutants emitted in source effluents, e.g., gas from a smokestack, involves specific spectral measurements of infrared radiation and, in this method, includes ratioing the signals from two gas-reference cell pairs to eliminate dependencies upon the inlowering atmosphere and source effluent temperature. An instrument cell construction and assembly using a unique cells-within-a cell permits use of a single lens that insures common fields-of-view for both cell pairs; a triple chopping system uses tuning forks to alternately pass the incoming energy through the gas and reference cells eliminating the need for separate sync signal generators, and provides a high carrier frequency improving the signal-to-noise ratio of the sensor.

4 Claims, 6 Drawing Figures

METHOD FOR REMOTE MONITORING OF GASEOUS PRODUCTS

BACKGROUND OF THE INVENTION

Prior and existing remote measurement devices for remotely monitoring the concentration of a particular gas species in a gaseous mixture are based on techniques involving laser-induced Raman and fluorescent scattering, correlation spectrometers, and interferometers which techniques have serious drawbacks.

Data obtained using laser techniques is difficult to interpret due to interfering species and the intervening atmosphere.

The correlation spectrometer and interferometer, while quite specific, are unfortunately very dependent upon the temperature of the source effluent.

None of the existing methods, save for that of the instant invention, are thus satisfactory when it comes to, for example, measuring gaseus pollutants emitted from stationary sources such as smokestacks, which may be at a distance exceeding one kilometer.

SUMMARY OF THE INVENTION

The present invention is, in part, concerned with a new and unique method for remotely monitoring the concentration of a particular gas species in a gaseous mixture.

The invention will be fully described in the detailed disclosure which follows, taken together with the accompanying drawings wherein FIG. 1 is a schematic showing of the viewing geometry involved in remotely monitoring the pollutant contained in a smokestack plume;

PHYSICAL PRINCIPLE OF THE INVENTION

Figure 1:
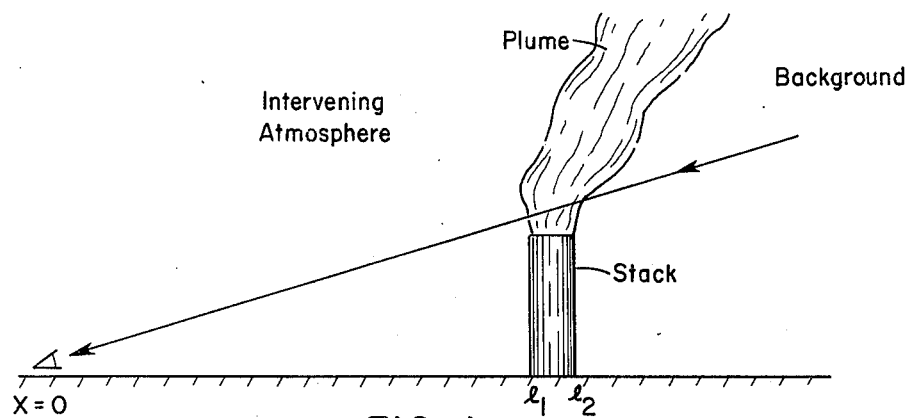

The phenomenology for the remote detection of pollutants emitted in source effluents is dependent upon specific spectral measurement of infrared radiation. From the basic theory of radiation transfer, an expression describing the monochromatic radiation received by the sensor from the background, the effluent plume, and the intervening atmosphere is:

$$E(\lambda) = \tau_c \tau_a \int_{\infty}^{l_2} N_b^{o'}(T_b(x)) \frac{\delta \tau_a'(x)}{\delta x} dx$$

$$+ \tau_a \int_{l_2}^{l_1} N_c^o(T_c(x)) \frac{\delta \tau_c(x)}{\delta x} dx$$

$$+ \int_{l_1}^{0} N_b^o(T_b(x)) \frac{\delta \tau_a}{\delta x} dx \quad (1)$$

where the first term is the emission of the atmosphere from infinity to the far edge of the plume; the second term is the emission of the plume and the third term is the emission of the atmosphere between the plume and the sensor, as shown in FIG. 1.

$N^o(T(x))$ represents the blackbody function at temperature T, which is, in general a function of $x$ along the line of sight and, of course, is also a function of wavelength $\lambda$. The atmospheric transmission is indicated by the terms $\tau_a$ and $\tau_a'$; it consists of the transmissivities of all of the normal atmospheric species, i.e., $$\tau_a = \tau(CO_2) \times \tau(H_2O) \times \tau(CH_4) \times \tau(N_2O) \quad (2)$$

The transmissivity of the plume is similarly formulated $$\tau_c = \tau(SO_2) \times \tau(CO_2) \times \tau(H_2O) \times \tau(N_2O) \times \tau(CH_4) \times \quad (3)$$

where the pollutant of interest is $SO_2$, for example. This may be written as $\tau_c = \tau \tau_i$, where $\tau$ is the transmissivity due to $SO_2$ and $\tau_i$ is the transmissivity of all interfering species. The $SO_2$ transmissivity $\tau$ is given by $$\tau = \exp - \int_{l_2}^{l_1} k(\lambda) C(x) p_t(x) dx \quad (4)$$

where $k(\lambda)$ is the spectral absorption coefficient of $SO_2$, C is the unknown $SO_2$ concentration in the plume and $p_t$ is the total pressure of the plume.

Consideration of Equations 1–4 shows that the task of quantifying the $SO_2$ concentration is complex. Thus the radiation received by the sensor is a function of the atmospheric and plume temperatures as well as the transmissivities of $SO_2$ and interfering species in the atmosphere and plume.

Figure 2:
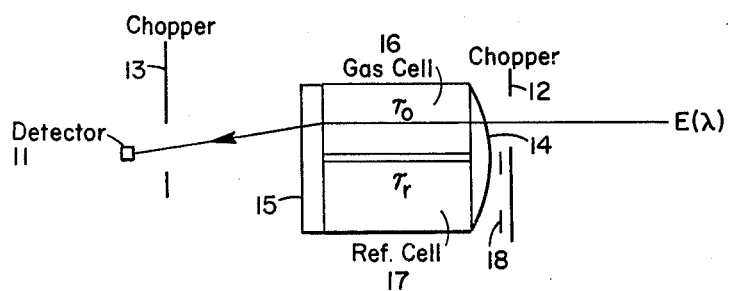
FIG. 2 is a schematic diagram of a sensor for remotely monitoring concentration of a particular gas species.

A schematic diagram of the remote sensor comprising the invention is shown in FIG. 2. The sensor comprises a detector II, a fore light chopper 12, an aft light chopper 13, lens 14, window 15, a gas cell 16 containing $SO_2$, the reference cell 17 containing $N_2$ or $N_2$ plus a smaller amount of $SO_2$, and an aperture adjustment 17a. The aft chopper 13, which operates at a higher frequency, provides an average of the radiation passing through both cells.

When the forward chopper is in the position indicated in FIG. 2, the signal generated at the detector is $$V_1 = \int_{\Delta \lambda} \left\{ E \tau_{14} \tau_o \tau_{15} + N_{12}^o \tau_{14} \tau_r \tau_{15} \right.$$

$$\left. + N_{ins}^O [\epsilon_{14}(\tau_o \tau_{15} + \tau_r \tau_{15}) + \epsilon_o \tau_{15} + (\epsilon_o + \epsilon_r) \tau_{15} + \epsilon_{15} + \epsilon_{13}] \right\} R d\lambda \quad (5)$$

where $\tau$, $N^o$ and $\epsilon$ refer to transmissivity, blackbody function and emissivity respectively; the numerical subscripts are indicated in FIG. 2 and it refers to the instrument which is maintained at a constant temperature; R is the overall responsivity of the detector, optical efficiency and electronics. All symbols are, of course, a function of $\lambda$, but this is not noted for the sake of brevity.

Similarly, when the forward chopper blocks off the gas cell, the signal generated at the detector is $$V_2 = \int_{\Delta\lambda} \Big\{ E\tau_{14}\tau_r\tau_{15} + N_{12}{}^o\tau_{14}\tau_o\tau_{15}$$

$$+ N \underset{\text{ins}}{O} [\epsilon_{14}(\tau_o\tau_{15} + \tau_r\tau_{15}) + \epsilon_r\tau_{15} + (\epsilon_r + \epsilon_o)\tau_{15} + \epsilon_{15} + \epsilon_{15}] \Big\} R d\lambda \quad (6)$$

The signal generated at the frequency of the forward chopper is the difference between $V_2$ and $V_1$:

$$\Delta V = \int_{\Delta\lambda} [\tau_r - \tau_o] [\tau_{14}\tau_{15}(E - \overline{N_{12}{}^o})] R d\lambda \quad (7)$$

The instrument is balanced, or zeroed, with $E=0$, by adjusting the aperture of the reference cell; that is, $$\int_{\Delta\lambda} \tau_{14}\tau_{15}N_{12}(\tau_r - \tau_o) R d\lambda \quad (8)$$

Since R, $\tau_{14}$ and $\tau_{15}$ are only slowly varying functions of $\lambda$ an overall effective responsivity $R_o$ may be defined by $R_o = \overline{\tau_{14}\tau_{15}R}$ where the bar denotes the mean value over the interval $\Delta\lambda$. Thus, when $E \neq 0$ the ac signal is given by $$\frac{\Delta V}{R_o} = \int_{\Delta\lambda} E(\lambda) [\tau_r - \tau_o(\lambda)] d\lambda \quad (9)$$

where $E(\lambda)$ is given by Eq. 1.

When $E(\lambda)$ from Eq. (1) is introduced into Eq. (9) and the integration over $\Delta\lambda$ carried out, one obtains $$\frac{\Delta V}{R_o} = \bar{\tau}_i \overline{N_a{}^o}' (\bar{\tau}_a - \overline{\tau_a\tau_a}') (\overline{\tau\tau}_r - \overline{\tau\tau}_o)$$

$$+ \overline{N_c{}^o} [\bar{\tau}_a(\tau_r - \bar{\tau}_o) + \bar{\tau}_a\bar{\tau}_i(\overline{\tau\tau}_o - \overline{\tau\tau}_r)]$$

$$+ \overline{N_a{}^o}(1 - \bar{\tau}_a)(\tau_r - \bar{\tau}_o) \quad (10)$$

Since by balancing the instrument, $\bar{\tau}_o = \bar{\tau}_r$, Eq. 10 may be simplifed:

$$\frac{\Delta V}{R_o} = \bar{\tau}_i [\bar{\tau}_a \overline{N_c{}^o} - (\bar{\tau}_a - \overline{\tau_a\tau_a}') \overline{N_a{}^o}'] (\overline{\tau\tau}_o - \overline{\tau\tau}_r) \quad (11)$$

Thus, an expression results that shows the ac signal is effectively a product of a modulation function that is only related to the SO$_2$ transmissivity fixed instrument transmissivities, and the difference between the radiance emitted by the plume and background atmosphere; it is non-linear with SO$_2$ concentration.

It is important to note that the modulation function is non-linear and its degree of non-linearity is strongly dependent upon the relative amounts of SO$_2$ in the gas and reference cells.

If we now consider a second cell pair with $\bar{\tau}'_o \neq \bar{\tau}_o$ and chopped at a different frequency, but using the same detector and optical components, a similar expression is derived:

$$\frac{\Delta V'}{R_o} = \bar{\tau}_i [\bar{\tau}_a \overline{N_c{}^o} - (\bar{\tau}_a - \overline{\tau_a\tau_a}') \overline{N_a{}^o}'] (\overline{\tau\tau}'_o - \overline{\tau\tau}'_r) \quad (12)$$

Note that the modulation function has a different non-linear response from that given in Eq. 11. The different modulation function responses are adjustable over a large range by varying the amounts of SO$_2$ placed in the specifying and reference cells.

Division of Eq. 11 by Eq. 12 gives $$\frac{\Delta V}{\Delta V'} = \frac{\overline{\tau\tau}_o - \overline{\tau\tau}_r}{\overline{\tau\tau}'_o - \overline{\tau\tau}'_r} \quad (13)$$

which is only dependent upon known instrument transmissivities and the transmissivity of the gas to be detected. And, it is completely independent of o plume radiance
o atmospheric radiance
o intervening atmospheric transmissivity
o instrument spectral responsivity.

THE SENSOR

Figure 3:
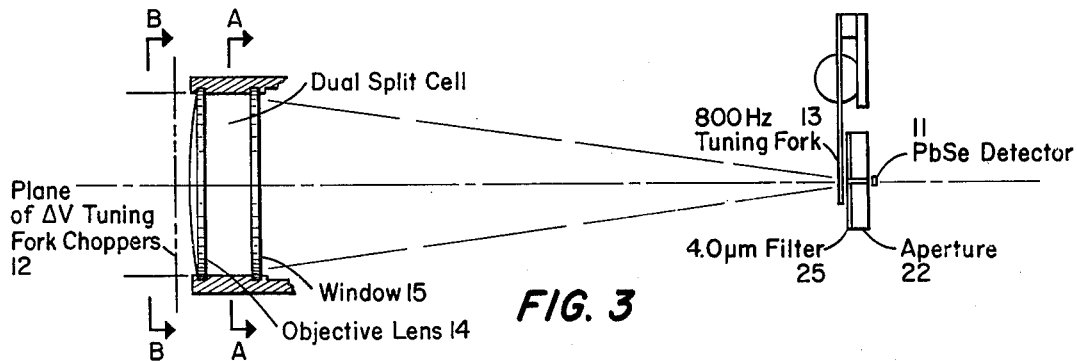
FIG. 3 is a schematic showing of an optical system utilized in practicing the method of the present invention.

As illustrated in FIG. 3, the two-cell pair sensor is contained in a single optical system. Separate tuning fork choppers 12a and 12b are used for each cell pair. The objective lens 14 serves as the front window of the dual split cell 19. A flat window 15 seals the rear of the cell 19.

The image of the stack plume is focused on an aperture 21 which defines the field of view. The aperture 21 is a round polished hole through a plate approximately 0.5 cm thick.

An ambient temperature operation (ATO) PbSe detector 11 is located immediately behind the aperture 21. Because the plate is thick compared to the diameter of the rapidly diverging beam 22 it acts like a parallel light pipe, and the resulting multiple reflections cause a diffused image to fall on the detector 11, thereby reducing the effect of non-uniform detector responsivity. A pass band optical filter 25 is located at the entrance of the aperture 21. This filter is centered at 4.00 microns with a half-transmission width of 0.2 microns for the case in which SO$_2$ is the species to be monitored. Other species of course require different optical filters.

Figure 4:
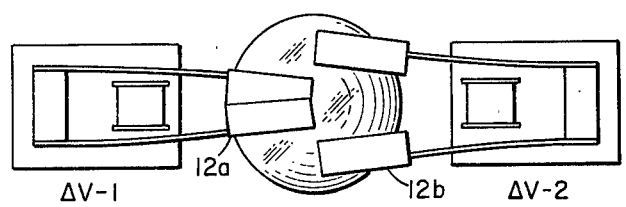
FIG. 4 illustrates the dual tuning fork configuration useable in practicing the method of this invention.

FIG. 4 shows the configuration of the dual split cell. The two gas cells, 16a and 16b of FIG. 4, contain different partial pressures of SO$_2$ and are pressurized to 1 atm with pure N$_2$ to pressure-broaden the SO$_2$ lines.

The reference cells 17a, 17b, 17c, and 17d contain only a small amount of SO$_2$ and are also pressurized to one atmosphere with pure N$_2$. Adjustments 18 in the reference cells 17a, 17b, 17c, and 17d allow adjustment (balance) of the reference cell transmission to equal that of the corresponding gas cell.

The tuning fork choppers 12a and 12b are stable, reliable and low power. Because the frequency is dependent only on the mechanical resonance of the fork, no stable-frequency AC power source is needed and battery operation is possible as is true of the entire electronics system.

Figure 5:
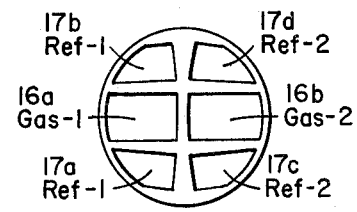
FIG. 5 is a section through A—A of FIG. 3, showing the configuration of the dual split cell of a device used in carrying out the method.

FIG. 5 shows the dual tuning fork configuration. Fork 12a is shown closed, allowing radiation to pass through the $\Delta V$-1 reference cells 17a and 17b; Fork 12b is shown open, allowing radiation to pass through the $\Delta V$-2 gas cell 16b. Fork 12a operates a frequency of 40 Hz and fork 12b at a frequency of 100 Hz. Because a single lens serves both $\Delta V$-1 and $\Delta V$-2 systems and superimposes the image of each on the same detector aperture, both systems have exactly the same field of view at the stack plume, as is essential for proper cancellatin of the stack effluent temperature factor. The superimposed image signals of the two $\Delta V$ systems are electronically separated by signal processing described later.

A third tuning fork chopper 13, operating at 800 Hz, is located immediately ahead of the detector aperture. This chopper obstructs the entire beam when closed. The purpose of this chopper is to eliminate the low frequency $1/f$ detector noise from the $\Delta V$ signals. Its operation is described later.

A 4-power Bushnell riflescope (not shown) accurately aligned with the GFC optics, is an integral part of the device to permit accurate aiming. An illuminated reticle in the riflescope will permit accurate aiming at dusk or under other adverse lighting conditions.

Figure 6:
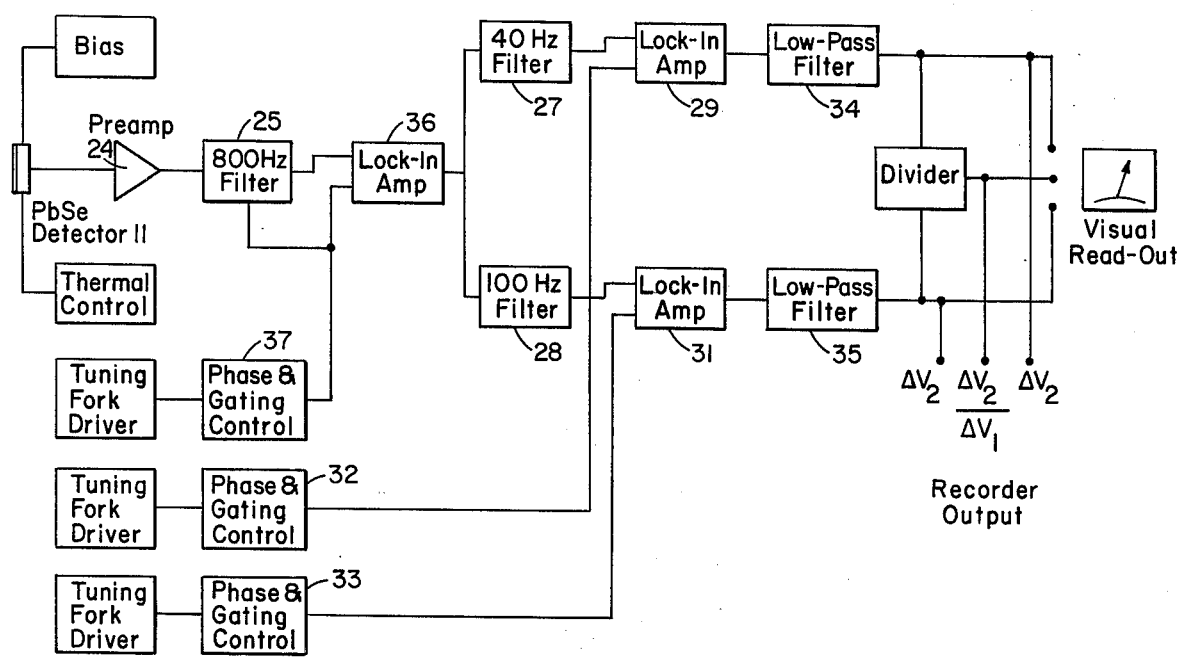
FIG. 6 is a block diagram of the signal processing system of the invention.

The electronic signal processing technique involves phasing, gating (sample-hold) and ratioing of different frequency signals. A block diagram of the signal processing system is shown in FIG. 6.

In this device, two $\Delta V$ signals are generated. These result from the two gas/reference cells systems containing different partial pressures of $SO_2$. Each cell pair is chopped by a tuning fork chopper of different frequency. Because of the common objective lens the image at the detector consists of both $\Delta V$ signals at their respective chopping frequencies. These are later separated by electronic filtering. The frequencies are 40 Hz and 100 Hz. These are not harmonically related and are far enough apart to allow good separation by filtering, yet are low compared with the 800 Hz "carrier" system created by the third chopper 13 described hereinafter. This tuning fork chopper 13 operating at 800 Hz is located immediately in front of the aperture plate and obstructs the entire light beam when closed. The detector signal is therefore the 800 Hz carrier signal amplitude modulated by the two $\Delta V$ chopper frequencies.

The detector 11 is followed by a preamp 24 and an 800 Hz bandpass filter. The filter 25 passes the 800 signal and its modulation at 700, 760, 840, and 900 Hz while rejecting the DC component of the detector output which is due to the bias current. Thus, even though low frequency $\Delta V$ chopping is used to obtain large-amplitude fork oscillations, only the detector noise at the 800 Hz passband is processed, and the large $1/f$ detector noise at the low $\Delta V$ chopping frequencies is rejected and high effective detector $D*$'s are obtained.

The filter output feeds a lock-in amplifier 36. Receiving its reference signal from the 800 Hz fork phase and gating circuit 37 the lock-in synchronously detects the 800 Hz wavetrain and provides a DC output on which are superimposed the two $\Delta V$ signals.

Two bandpass filters, operating at the $\Delta V$ frequencies, separate the signals into $\Delta V-1$ and $\Delta V-2$. Each is then detected by separate lock-in amplifiers 29 and 31 which are synchronized by phase and gating circuits 32 and 33 and the signals, after low-pass filtering 34 and 35, are the $\Delta V-1$ and $\Delta V-2$ output data.

$\Delta V-1$, $\Delta V-2$, and their ratio are selectively read out on a high-accuracy panel meter. In addition, all three are available at BNC connectors for recording or for DVM readout.

Referring now to further details of the foregoing, the detector 11 is, e.g., a 0.4 mm × 0.4 mm lead selenide photoconductive cell, operating at ambient temperature. Because of the small size and high operating frequency (800 Hz) the detectivity is approximately $D* = 10^{10}$ cm − Hz ½ W−1. The time constant of several microseconds permits a 800 Hz chopping without loss of signal. An ambient temperature operation (ATO) detector is chosen since detector cooling may not be practical, e.g. in a portable battery-operated instrument. The detector is maintained at a stable temperature to prevent signal variations due to thermally-induced changes in the detector responsibility. The detector bias current is provided by a low-noise regulated supply. The small detector size allows the use of low bias voltage while maintaining the high electric field needed for efficient electron collection.

The preamplifier 24 is a conventional FET-input design.

The 800 Hz filter 25 is designed to pass the 800 Hz radiometric V signal and its $\Delta V$ modulation sidebands. The lock-in amplifier 36 consists of two sample-and-hold circuits, one sampling during the greater amplitude half cycle and the other 180° out of phase; the two values are subtracted to get the peak-to-peak value.

$\Delta V$ Bandpass filters and synchronous detectors: The signal processing for the $\Delta V$ signals are identical except for operating frequency, $f(\Delta V-1)=40$ Hz and $f(\Delta V-2)=100$ Hz. Bandpass filters at the respective $\Delta V$ frequencies will separate the two $\Delta V$ signals.

The $\Delta V$ lock-ins are the same as used at 800 Hz. The lock-in outputs are the unfiltered $\Delta V-1$ and $\Delta V-2$ data.

Output filters (low pass filters) are of conventional design. Variable time constants provide a readout of 99% in 1, 3, 10, 30 and 90 seconds.

A commercially available suitable divider circuit is used, such as Type 433J, Analog Devices Inc., Norwood, Mass.

We claim:

1. A method for remotely monitoring the concentration of a particular gas species in a gaseous mixture which comprises passing the radiation from a distant source comprising the gaseous mixture through a sensor which comprises a detector, two forward and one aft chopper, a lens, specifying gas cells containing the gas species to be monitored and a reference cell containing a smaller amount of the particular gas; the first forward chopper alternately passing the entering radiation through the first cell pair comprising the gas cell containing the gas species being monitored and the reference cell, the aft chopper, operating at a higher frequency, providing an average of the radiation passing through both cells, whereby to generate a first signal at the detector; simultaneously passing the said radiation from the said distant source through the second forward chopper and the second cell pair comprising a specifying gas cell containing a different concentration of the gas species being monitored and the same reference cell aft while chopping it at a different frequency but using the same aft detector, and optical components to generate a second signal at the detector; the said ratio of the two signals being dependent only on the known transmissivities of the gas concentrations in the sensors and the transmissivity of the gas to be detected.

2. The method of claim 1 wherein the gaseous mixture comprises smokestack effluent.

3. The method of claim 1 wherein the said gas species is infrared active.

4. The method of claim 1 wherein the said gas species is sulfur dioxide.

* * * * *